(12) United States Patent
Ryu et al.

(10) Patent No.: US 12,144,799 B2
(45) Date of Patent: Nov. 19, 2024

(54) METHOD FOR LONG-TERM STORAGE OF CHLOROPHYLL-CONTAINING EXTRACT

(71) Applicant: ABL CO., LTD, Gwangju (KR)

(72) Inventors: Byung Ju Ryu, Gwangju (KR); Jihwan Im, Gwangju (KR); Hyoungmin Yeo, Gwangju (KR); Myungeun Lee, Gwangju (KR); Chulcuy Choi, Gwangju (KR)

(73) Assignee: ABL CO., LTD, Gwangju (KR)

( * ) Notice: Subject to any disclaimer, the term of this patent is extended or adjusted under 35 U.S.C. 154(b) by 670 days.

(21) Appl. No.: 17/290,839

(22) PCT Filed: Nov. 6, 2019

(86) PCT No.: PCT/KR2019/014999
§ 371 (c)(1),
(2) Date: May 3, 2021

(87) PCT Pub. No.: WO2020/096354
PCT Pub. Date: May 14, 2020

(65) Prior Publication Data
US 2021/0401801 A1    Dec. 30, 2021

(30) Foreign Application Priority Data

Nov. 6, 2018   (KR) ........................ 10-2018-0134973

(51) Int. Cl.
| | | |
|---|---|---|
| *A23L 33/105* | (2016.01) | |
| *A23L 3/3463* | (2006.01) | |
| *A23L 33/12* | (2016.01) | |
| *A61K 31/409* | (2006.01) | |
| *A61K 36/00* | (2006.01) | |
| *A61K 47/12* | (2006.01) | |
| *A61K 47/44* | (2017.01) | |

(52) U.S. Cl.
CPC .......... *A61K 31/409* (2013.01); *A23L 3/3463* (2013.01); *A23L 33/105* (2016.08); *A23L 33/12* (2016.08); *A61K 36/00* (2013.01); *A61K 47/12* (2013.01); *A61K 47/44* (2013.01); *A23V 2002/00* (2013.01); *A61K 2236/37* (2013.01)

(58) Field of Classification Search
None
See application file for complete search history.

(56) References Cited

U.S. PATENT DOCUMENTS

2011/0256282 A1    10/2011   Piechocki et al.

FOREIGN PATENT DOCUMENTS

| | | | |
|---|---|---|---|
| EP | 3 808 360 | A1 | 4/2021 |
| KR | 10-2009-0032413 | A | 4/2009 |
| KR | 10-1032459 | B1 | 5/2011 |
| KR | 10-2012-0107061 | A | 9/2012 |
| KR | 10-1428486 | B1 | 8/2014 |
| KR | 10-2015-0116196 | A | 10/2015 |
| KR | 101873465 | * | 10/2016 |
| KR | 10-1873465 | B1 | 7/2018 |
| WO | WO 2010/120923 | A1 | 10/2010 |
| WO | WO 2014/023917 | A1 | 2/2014 |
| WO | WO 2017/159949 | A1 | 9/2017 |

OTHER PUBLICATIONS

International Search Report for PCT/KR2019/014999 mailed on Mar. 10, 2020.
European Search Report For EP19882102.7 issued on Jun. 27, 2022 from European patent office in a counterpart European patent application.
European Search Report For EP19882102.7 issued on Aug. 20, 2024 from European patent office in a counterpart European patent application.

* cited by examiner

*Primary Examiner* — Melissa S Mercier
(74) *Attorney, Agent, or Firm* — The PL Law Group, PLLC

(57) ABSTRACT

A method for long-term storage of chlorophyll which is unstable in the surrounding environment, according to an embodiment of the disclosure, includes dissolving a chlorophyll in oil having an unsaturated lipid structure to allow the chlorophyll to be included in the oil. A stabilizer employing oils having long-chain unsaturated lipid structures is used to stabilize chlorophyll.

11 Claims, 12 Drawing Sheets

FIG. 6

CHLOROPHYLL A CONTENT CHANGE BY PERIOD
(SQUALENE STABILIZATION, UNIT ppm)

| STORAGE PERIOD | 0 DAY | 10 DAY | 20 DAY | 1 MONTH | 2 MONTH | 3 MONTH | 4 MONTH | 5 MONTH | 6 MONTH | 7 MONTH | 8 MONTH | 9 MONTH | 10 MONTH | 11 MONTH | 12 MONTH |
|---|---|---|---|---|---|---|---|---|---|---|---|---|---|---|---|
| FREEZING TEMPERATURE (-20°C) | 213 | 213 | 212 | 211 | 210 | 209 | 207 | 206 | 205 | 204 | 203 | 201 | 200 | 199 | 198 |
| REFRIGERATING TEMPERATURE (4°C) | 213 | 210 | 208 | 206 | 200 | 194 | 188 | 183 | 177 | 172 | 167 | 162 | 157 | 153 | 148 |
| ROOM TEMPERATURE (25°C) | 213 | 201 | 194 | 180 | 158 | 132 | 111 | 98 | 88 | 76 | 64 | 56 | 47 | 42 | 34 |
| HIGH TEMPERATURE (50°C) | 213 | 140 | 99 | 72 | 18 | 5.7 | 1.7 | 0.5 | - | - | - | - | - | - | - |
| LEFT AT ROOM TEMPERATURE | 213 | 207 | 201 | 195 | 180 | 165 | 148 | 135 | 115 | 98 | 85 | 75 | 70 | 68 | 64 |

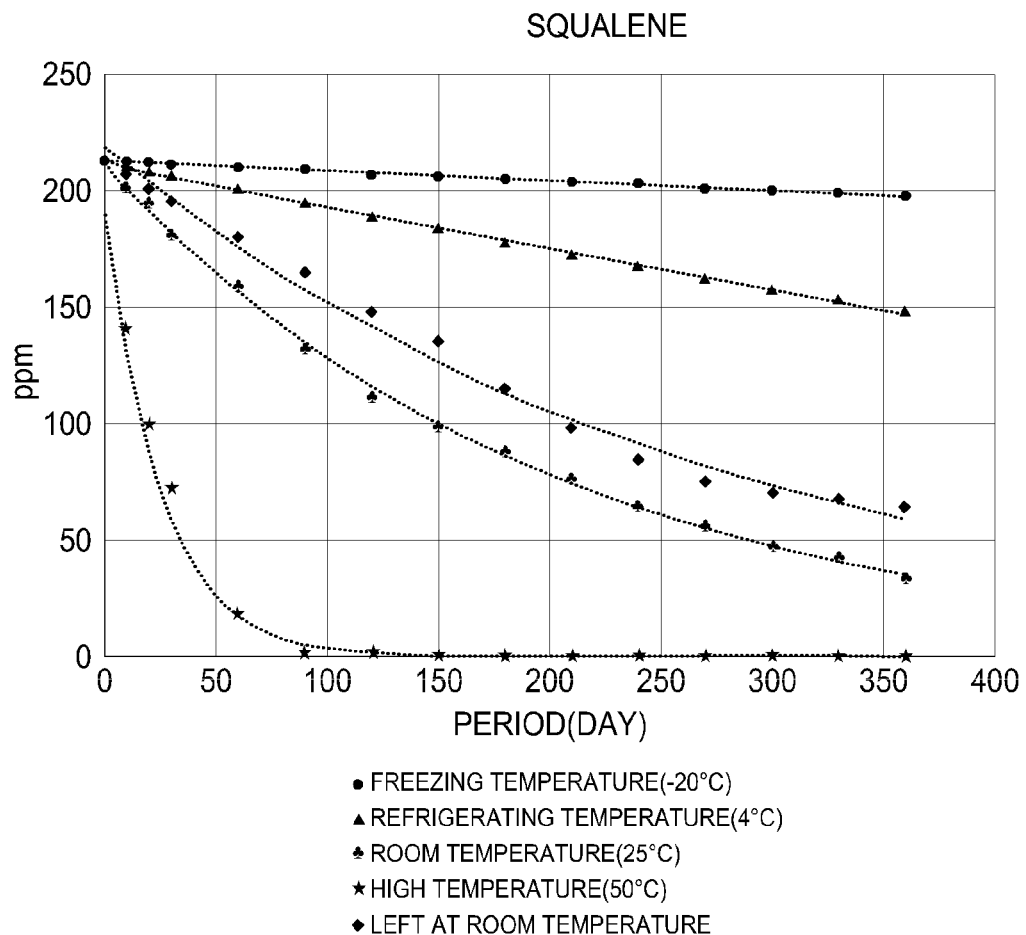

- FREEZING TEMPERATURE(-20°C)
- REFRIGERATING TEMPERATURE(4°C)
- ROOM TEMPERATURE(25°C)
- HIGH TEMPERATURE(50°C)
- LEFT AT ROOM TEMPERATURE

FIG. 7

CHLOROPHYLL A CONTENT CHANGE BY PERIOD
(SOYBEAN OIL STABILIZATION, UNIT ppm)

| STORAGE PERIOD | 0 DAY | 10 DAY | 20 DAY | 1 MONTH | 2 MONTH | 3 MONTH | 4 MONTH | 5 MONTH | 6 MONTH | 7 MONTH | 8 MONTH | 9 MONTH | 10 MONTH | 11 MONTH | 12 MONTH |
|---|---|---|---|---|---|---|---|---|---|---|---|---|---|---|---|
| FREEZING TEMPERATURE (-20°C) | 121 | 118 | 111 | 102 | 95 | 88 | 74 | 66 | 59 | 52 | 43 | 41 | 36 | 29 | 28 |
| REFRIGERATING TEMPERATURE (4°C) | 121 | 117 | 109 | 105 | 89 | 81 | 66 | 57 | 50 | 42 | 33 | 31 | 27 | 23 | 21 |
| ROOM TEMPERATURE (25°C) | 121 | 104 | 90 | 77 | 50 | 31 | 20 | 12 | 8 | 5 | 3 | 2 | 1 | 0.8 | 0.5 |
| HIGH TEMPERATURE (50°C) | 121 | 67 | 37 | 20 | 11 | 6 | 4 | - | - | - | - | - | - | - | - |
| LEFT AT ROOM TEMPERATURE | 121 | 110 | 98 | 92 | 70 | 55 | 42 | 25 | 19 | 8 | 5 | 3 | 2 | 1 | 1 |

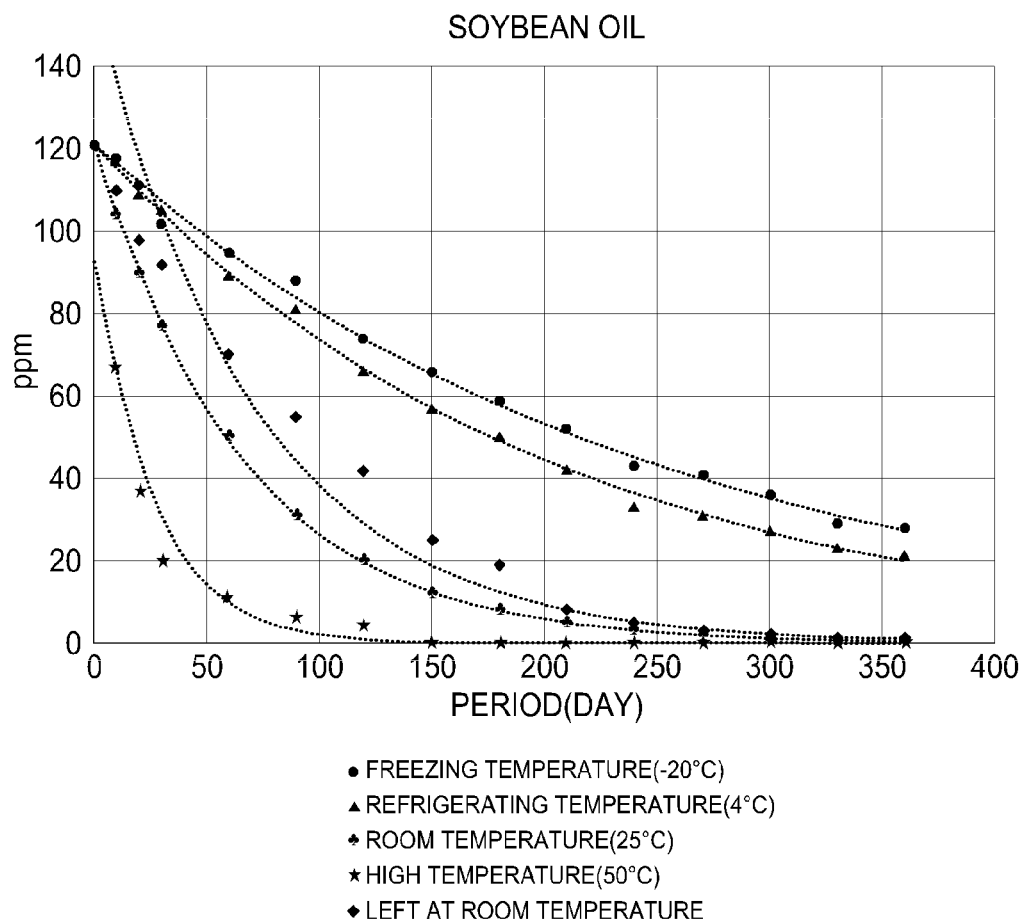

SOYBEAN OIL

- FREEZING TEMPERATURE(-20°C)
- REFRIGERATING TEMPERATURE(4°C)
- ROOM TEMPERATURE(25°C)
- HIGH TEMPERATURE(50°C)
- LEFT AT ROOM TEMPERATURE

FIG. 8

CHLOROPHYLL A CONTENT CHANGE BY PERIOD
(CANOLA OIL STABILIZATION, UNIT ppm)

| STORAGE PERIOD | 0 DAY | 10 DAY | 20 DAY | 1 MONTH | 2 MONTH | 3 MONTH | 4 MONTH | 5 MONTH | 6 MONTH | 7 MONTH | 8 MONTH | 9 MONTH | 10 MONTH | 11 MONTH | 12 MONTH |
|---|---|---|---|---|---|---|---|---|---|---|---|---|---|---|---|
| FREEZING TEMPERATURE (-20°C) | 120 | 117 | 115 | 114 | 109 | 104 | 100 | 96 | 92 | 88 | 85 | 81 | 78 | 74 | 70 |
| REFRIGERATING TEMPERATURE (4°C) | 120 | 116 | 113 | 111 | 104 | 97 | 91 | 85 | 80 | 74 | 70 | 65 | 61 | 57 | 54 |
| ROOM TEMPERATURE (25°C) | 120 | 105 | 93 | 83 | 57 | 40 | 28 | 19 | 13 | 9 | 6 | 4 | 3 | - | - |
| HIGH TEMPERATURE (50°C) | 120 | 63 | 35 | 20 | 3 | - | - | - | - | - | - | - | - | - | - |
| LEFT AT ROOM TEMPERATURE | 120 | 110 | 107 | 98 | 82 | 71 | 61 | 41 | 33 | 21 | 18 | 17 | 14 | 12 | 9 |

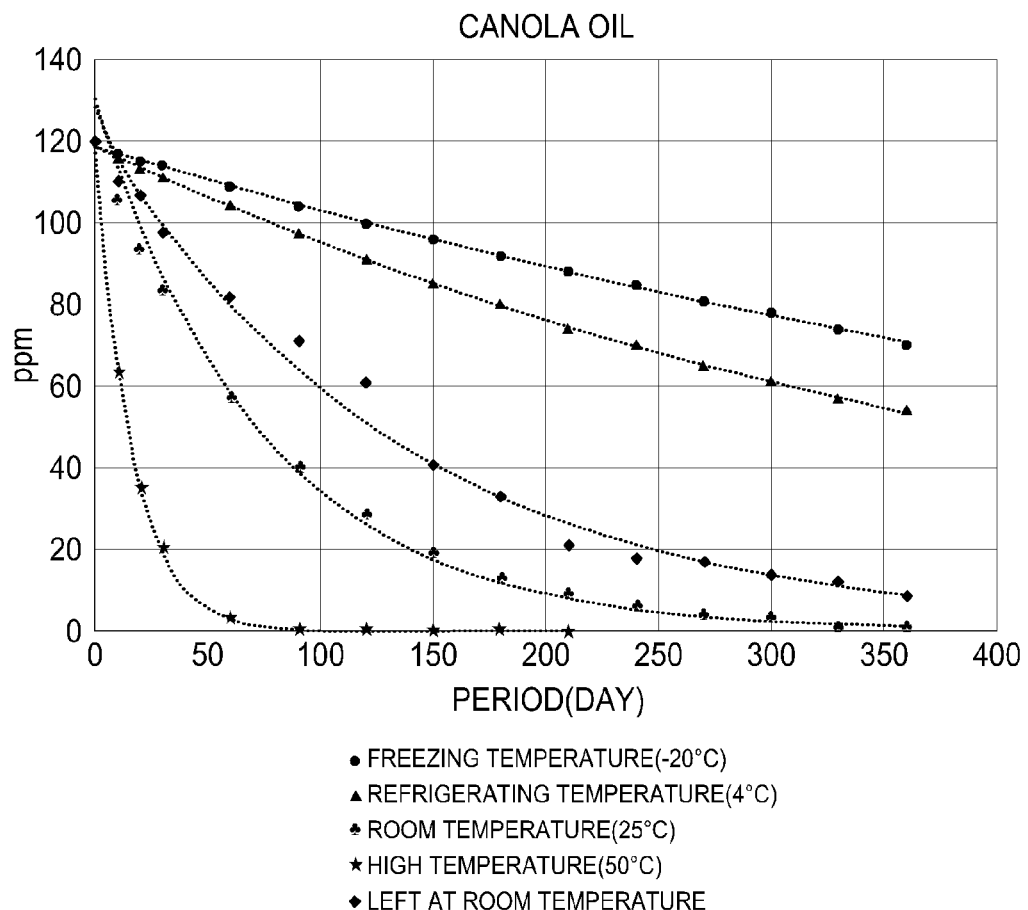

CANOLA OIL

- FREEZING TEMPERATURE(-20°C)
- REFRIGERATING TEMPERATURE(4°C)
- ROOM TEMPERATURE(25°C)
- HIGH TEMPERATURE(50°C)
- LEFT AT ROOM TEMPERATURE

CHLOROPHYLL A CONTENT CHANGE BY PERIOD
(SUNFLOWER SEED OIL STABILIZATION, UNIT ppm)

| STORAGE PERIOD | 0 DAY | 10 DAY | 20 DAY | 1 MONTH | 2 MONTH | 3 MONTH | 4 MONTH | 5 MONTH | 6 MONTH | 7 MONTH | 8 MONTH | 9 MONTH | 10 MONTH | 11 MONTH | 12 MONTH |
|---|---|---|---|---|---|---|---|---|---|---|---|---|---|---|---|
| FREEZING TEMPERATURE (-20°C) | 122 | 119 | 117 | 114 | 108 | 101 | 95 | 92 | 85 | 80 | 75 | 71 | 67 | 63 | 60 |
| REFRIGERATING TEMPERATURE (4°C) | 122 | 121 | 120 | 116 | 109 | 102 | 97 | 89 | 81 | 78 | 73 | 69 | 64 | 61 | 57 |
| ROOM TEMPERATURE (25°C) | 122 | 118 | 110 | 102 | 90 | 77 | 64 | 57 | 45 | 42 | 37 | 29 | 27 | 23 | 20 |
| HIGH TEMPERATURE (50°C) | 122 | 79 | 51 | 33 | 9 | 2 | - | - | - | - | - | - | - | - | - |
| LEFT AT ROOM TEMPERATURE | 122 | 118 | 115 | 112 | 105 | 93 | 85 | 77 | 65 | 62 | 55 | 49 | 45 | 43 | 39 |

FIG. 10

CHLOROPHYLL A CONTENT CHANGE BY PERIOD
(GRAPESEED OIL STABILIZATION, UNIT ppm)

| STORAGE PERIOD | 0 DAY | 10 DAY | 20 DAY | 1 MONTH | 2 MONTH | 3 MONTH | 4 MONTH | 5 MONTH | 6 MONTH | 7 MONTH | 8 MONTH | 9 MONTH | 10 MONTH | 11 MONTH | 12 MONTH |
|---|---|---|---|---|---|---|---|---|---|---|---|---|---|---|---|
| FREEZING TEMPERATURE (-20°C) | 117 | 112 | 111 | 110 | 103 | 97 | 72 | 86 | 81 | 76 | 73 | 68 | 64 | 60 | 56 |
| REFRIGERATING TEMPERATURE (4°C) | 117 | 112 | 111 | 109 | 103 | 96 | 90 | 85 | 80 | 75 | 59 | 66 | 63 | 58 | 54 |
| ROOM TEMPERATURE (25°C) | 117 | 100 | 95 | 87 | 66 | 49 | 37 | 28 | 21 | 15 | 13 | 8 | - | - | - |
| HIGH TEMPERATURE (50°C) | 117 | 55 | 38 | 13 | - | - | - | - | - | - | - | - | - | - | - |
| LEFT AT ROOM TEMPERATURE | 117 | 106 | 103 | 94 | 85 | 72 | 62 | 55 | 52 | 49 | 48 | 45 | 41 | 35 | 32 |

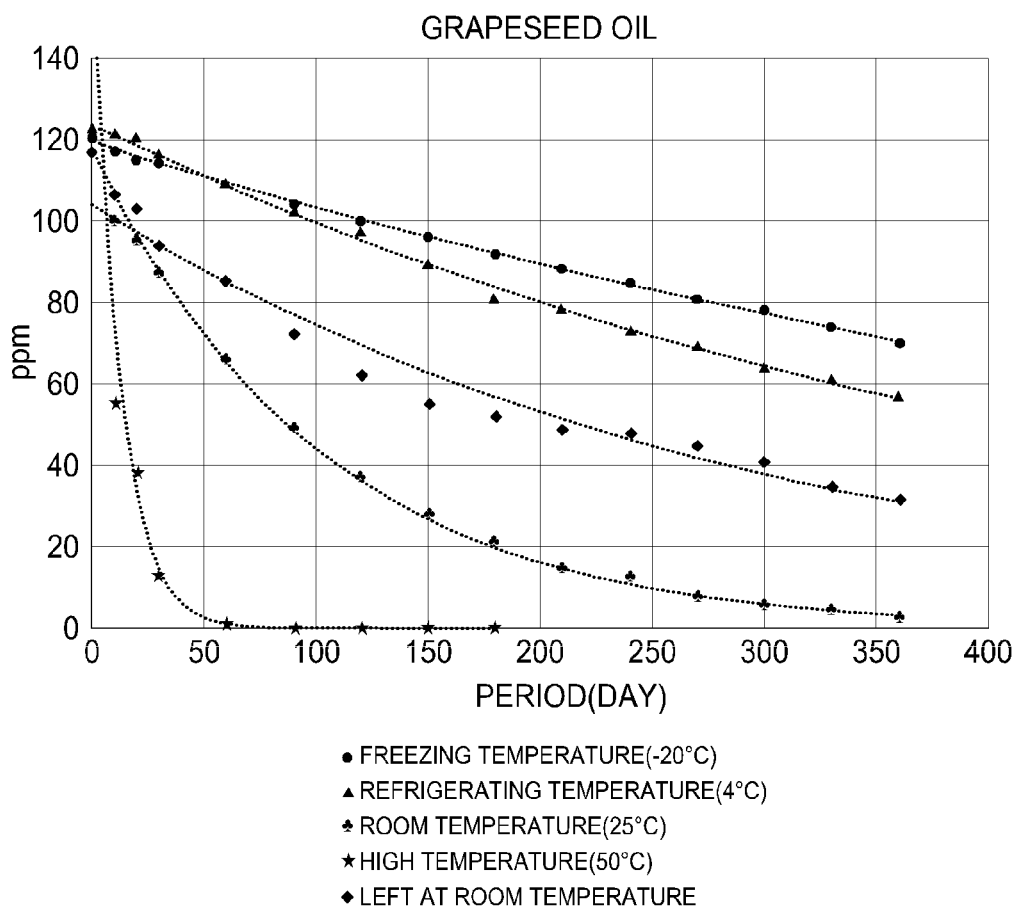

- FREEZING TEMPERATURE(-20°C)
- REFRIGERATING TEMPERATURE(4°C)
- ROOM TEMPERATURE(25°C)
- HIGH TEMPERATURE(50°C)
- LEFT AT ROOM TEMPERATURE

CHLOROPHYLL A CONTENT CHANGE BY PERIOD
(OLIVE OIL STABILIZATION, UNIT ppm)

| STORAGE PERIOD | 0 DAY | 10 DAY | 20 DAY | 1 MONTH | 2 MONTH | 3 MONTH | 4 MONTH | 5 MONTH | 6 MONTH | 7 MONTH | 8 MONTH | 9 MONTH | 10 MONTH | 11 MONTH | 12 MONTH |
|---|---|---|---|---|---|---|---|---|---|---|---|---|---|---|---|
| FREEZING TEMPERATURE (-20°C) | 113 | 109 | 108 | 106 | 102 | 98 | 92 | 88 | 85 | 79 | 75 | 73 | 69 | 64 | 62 |
| REFRIGERATING TEMPERATURE (4°C) | 113 | 111 | 109 | 106 | 99 | 93 | 87 | 82 | 77 | 72 | 67 | 65 | 60 | 56 | 53 |
| ROOM TEMPERATURE (25°C) | 113 | 98 | 91 | 80 | 60 | 45 | 32 | 21 | 15 | 10 | 7 | 5 | 3 | 2 | - |
| HIGH TEMPERATURE (50°C) | 113 | 62 | 45 | 31 | 8 | 2 | - | - | - | - | - | - | - | - | - |
| LEFT AT ROOM TEMPERATURE | 113 | 101 | 101 | 90 | 72 | 58 | 40 | 29 | 23 | 18 | 15 | 12 | 9 | 7 | 5 |

CHLOROPHYLL A CONTENT CHANGE BY PERIOD
(COCONUT OIL STABILIZATION, UNIT ppm)

| STORAGE PERIOD | 0 DAY | 10 DAY | 20 DAY | 1 MONTH | 2 MONTH | 3 MONTH | 4 MONTH | 5 MONTH | 6 MONTH | 7 MONTH | 8 MONTH | 9 MONTH | 10 MONTH | 11 MONTH | 12 MONTH |
|---|---|---|---|---|---|---|---|---|---|---|---|---|---|---|---|
| FREEZING TEMPERATURE (-20°C) | 115 | 109 | 106 | 99 | 83 | 72 | 64 | 58 | 46 | 39 | 34 | 30 | 26 | 22 | 21 |
| REFRIGERATING TEMPERATURE (4°C) | 115 | 103 | 64 | 82 | 63 | 42 | 30 | 23 | 16 | 12 | 8 | 6 | 4 | 3 | 2 |
| ROOM TEMPERATURE (25°C) | 115 | 92 | 77 | 63 | 34 | 19 | 10 | 6 | 3 | 1 | - | - | - | - | - |
| HIGH TEMPERATURE (50°C) | 115 | 70 | 43 | 26 | 4 | - | - | - | - | - | - | - | - | - | - |
| LEFT AT ROOM TEMPERATURE | 115 | 101 | 101 | 90 | 72 | 58 | 40 | 29 | 23 | 18 | 15 | 12 | 9 | 7 | 5 |

METHOD FOR LONG-TERM STORAGE OF CHLOROPHYLL-CONTAINING EXTRACT

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2019/014999, filed Nov. 6, 2019, which claims priority to the benefit of Korean Patent Application No. 10-2018-0134973 filed in the Korean Intellectual Property Office on Nov. 6, 2018, the entire contents of which are incorporated herein by reference.

BACKGROUND

1. Technical Field

The present invention relates to a method for long-term storage of chlorophyll, which is unstable in the surrounding environment, wherein a stabilizer employing oils having long-chain unsaturated lipid structures, of which squalene is representative, is used to stabilize chlorophyll.

2. Background Art

Unlike synthetic pigments which have toxicity and carcinogenicity, natural pigments derived from food have a variety of physiologically active ingredients such as vitamins, minerals, and polyphenol compounds, and are also safe, so the preference and demand therefor are increasing. Chlorophyll, which is a natural pigment obtainable from vegetables and fruits and widely used in the food industry, has a form in which magnesium (Mg) ions are bonded to the center of a porphyrin ring, and may be classified into types such as chlorophyll a, b, c, and d. In addition, chlorophyll varies in content, depending on the variety, cultivation soil, and harvest time of a plant from which the chlorophyll is extracted, and is affected by heat, light, oxygen, acids, enzymes, and the like, and thus, has some drawbacks in terms of quality and customer satisfaction.

Chlorophyll and chlorophyll derivatives show a variety of physiological activities, and thus, have been studied in various fields such as wound therapy, anti-inflammatory treatment and chemotherapy. Among the chlorophyll derivatives, chlorine e-6 plays an important role as a photosensitizer in photodynamic therapy, and copper chlorophyllin sodium is also used for the purpose of removing body odor, treating inflammation, and the like.

Types of such chlorophyll derivatives may be divided into pheophytin and pyropheophytin series in which a magnesium metal in the center has been substituted or removed, chlorophyllide and pheophorbide series in which a magnesium metal and phytol are removed, and chlorine series produced through a saponification reaction.

In 1960, a synthesis team of 17 post-doctoral researchers led by Professor Woodward successfully synthesized chlorophyll a, but the process thereof is quite complicated and long, and thus, is not suitable for commercial use.

As a typical method for extracting chlorophyll in plants, there is a method for performing extraction using various organic solvents such as acetone, ethanol, hexane, and dioxane, and then removing impurities through centrifugation, low-temperature immersion, and the like. However, there is a problem in that the method uses a solvent that is not allowed for food and medicine. Thus, in order to solve the above problem, there have been efforts to use and apply ethanol to food and the like. However, there is a problem in that an excessive amount of ethanol is used in an impurity removal step or an extraction step. Also, there still remains a problem in that an organic solvent such as acetone is used to remove polar impurities after extraction.

Meanwhile, extraction using supercritical fluids has advantages such as high solubility, fast mass transfer and heat transfer, low viscosity, a high diffusion rate, and fast permeability to micro-pores due to low surface tension, and is an extraction method which may solve technical difficulties such as low efficiency, low quality, low speed, and adverse impact on the environment in typical processes such as reactions, decomposition, extraction, distillation, crystallization, absorption, adsorption, drying, and washing.

Supercritical fluid extraction may fundamentally prevent or minimize the generation of various pollution sources (air, water, and land) in a product production process, and may also fundamentally prevent harmfulness to human health and the environment, and thus, may bring economic benefits compared to typical product production technologies.

Korean Patent Registration No. 1428486 discloses a method for preparing chlorella extract using a supercritical fluid extraction method, but the extraction target and extraction method thereof are different from those of a method for preparing chlorophyll-containing extract using a supercritical fluid extraction method for the present invention.

Meanwhile, since chlorophyll is greatly unstable in the surrounding environment, the applicability thereof was limited and it was hard to be applied to the food industry. At low pH, that is, in an acidic condition, a demetallation reaction occurs in which magnesium is removed, and at high pH, that is, in a basic condition, a saponification reaction occurs in which phytol is removed. When chlorophyll is exposed to oxygen in the air, a decoloration reaction occurs in which a porphyrin ring is open due to an oxidation reaction to destroy the structure of chlorophyll. In addition, the structure of chlorophyll is decomposed and destroyed by various enzymes that break down chlorophyll present in plants. Further, chlorophyll has a structure destroyed when being excited in an unstable state by light-induced electron energy transfer between chlorophyll dissolved in a solution. In particular, the higher the temperature, the faster the reaction rate.

When chlorophyll is dissolved in a solution, the structure of chlorophyll is easily denatured due to the electron transfer induced by light energy, and even when light is blocked, it is observed that the structure of chlorophyll is naturally destroyed. Solid-state chlorophyll is known to form aggregates so as to prevent photo-induced electron transfer, but that is also quite unstable due to actions other than the photo-induced electron transfer.

For this reason, various efforts have been made to stabilize chlorophyll. Copper chlorophyllin sodium, which is similar to chlorophyll in physiological activities and relatively stable in aqueous solutions, is being taken as various health aids such as body odor removal. However, copper chlorophyllin sodium has a downside as being synthesized through several chemical reactions from natural chlorophyll. In addition, Korean Patent Laid-Open Publication No. 2009-0032413 discloses a method for stabilizing chlorophyll by having black soybeans and the like in contact with chlorophyll, but the method provides a relatively short stabilization period, and is not widely used due to the current laws and regulations that prevent chlorophyll from being added to beans and processed foods thereof.

Therefore, there is a great demand from the industry for a simple stabilization method that enables long-term storage of chlorophyll.

SUMMARY

The present invention provides a method for long-term storage of chlorophyll, which is unstable in the surrounding environment, wherein a stabilizer employing oils having long-chain unsaturated lipid structures, of which squalene is representative, is used to stabilize chlorophyll.

The present invention also provides achieving other objects that may be readily derived by those skilled in the art from the said objects and the overall description of the present specification.

In accordance with an embodiment of the present invention, a chlorophyll storage method includes a chlorophyll dissolving step of allowing chlorophyll to be included in oil having an unsaturated lipid structure.

In addition, the oil having an unsaturated lipid structure may be selected from the group consisting of docosahexaenoic acid (DHA), eicosapentaenoic acid (EPA), squalene, soybean oil, canola oil, sunflower seed oil, macadamia oil, peanut oil, grapeseed oil, pumpkin seed oil, flaxseed oil, linseed oil, olive oil, corn oil, safflower oil, sesame oil, pine-nut oil, conjugated linolenic acid, almond oil, peach seed oil, apricot seed oil, walnut oil, rapeseed oil, raspberry oil, bilberry seed oil, cranberry seed oil, pomegranate seed oil, sacha inchi oil and other fruit seed oils, sea buckthorn oil, chia oil, perilla oil, diacylglycerol (DAG) oil, plant-derived sources of omega 3, fermentation sources of eicosapentaenoic acid (EPA), fermentation sources of docosahexaenoic acid (DHA), fermentation sources of other omega 3, 6, 9 oil combinations including fish oil and krill oil, sources of gamma linolenic acid (GLA) and/or stearidonic acid (SA), coconut oil and a combination thereof.

In addition, sources of DHA or EPA above may be selected from the group consisting of fish oil, microorganisms, single cell sources, and vegetable oils.

In addition, sources of GLA above may be selected from the group consisting of fish oil, microorganisms, single cell sources, and vegetable oils.

Also, the microorganisms may be yeast.

Also, the vegetable oils may be selected from the group consisting of flaxseed oil, soybean oil, and canola oil.

Also, the vegetable oils may be selected from the group consisting of evening primrose oil, blackcurrant seed oil, borage oil, and echium oil.

In addition, the chlorophyll dissolving step may include the steps of:

(A) distilling a chlorophyll extract under reduced pressure to remove a solvent and solidify chlorophyll; and (B) dissolving the solidified chlorophyll in oil having an unsaturated lipid structure.

In addition, the chlorophyll dissolving step may include the steps of:

(C) adding the oil having an unsaturated lipid structure to the chlorophyll extract to prepare a mixture; and (D) separating layers of the mixture to perform fractional extraction.

In addition, in the chlorophyll storage method, chlorophyll dissolved in the oil may be stored in a dark place after the chlorophyll dissolving step.

In addition, in the chlorophyll storage method, the chlorophyll dissolved in the oil may be stored at −100 to 12° C., −90 to 8° C., or −80 to 5° C. after the chlorophyll dissolving step.

A stabilization index may be 15000 to 25315, 17000 to 25310, or 18500 to 25305.

Meanwhile, the chlorophyll extract used in the chlorophyll storage method for the present invention may be obtained through a chlorophyll-containing extract preparation method including a chlorophyll extraction step of performing complex supercritical extraction on chlorophyll-containing plants or microorganisms.

Also, the plants or microorganisms may be selected from the group consisting of woody leaves, woody buds, herbal stems, herbal leaves, herbal buds; cyanophyta, prochlorophyta, rhodophyta, chlorophyta, heterokontophyta, tribophyta, glaucophyta, chlorarachniophytes, euglenophyta, euglenoids, haptophyta, chrysophyta, cryptophyta, cryptomonads, dinophyta, dinoflagellata, pyrmnesiophyta, bacillariophyta, xanthophyta, eustigmatophyta, raphidophyta, phaeophyta, phytoplankton; blue-green bacteria such as *spirulina*; microalgae such as chlorella genus, *scenedesmus* genus, *dunaliella* genus, *chlamydomonas* genus, *haematococcus* genus, and *botryococcus* genus; and a combination thereof.

In addition, in the chlorophyll extraction step, a main solvent may be carbon dioxide, and a co-solvent may be ethanol.

Also, in the chlorophyll extraction step, the total flow rate of the complex supercritical extraction may be 20 to 120 ml/min, preferably 30 to 100 ml/min, and more preferably 40 to 85 ml/min.

Also, in the chlorophyll extraction step, the flow rate of the co-solvent of the complex supercritical extraction may be 1 to 20 ml/min, preferably 2 to 15 ml/min, and more preferably 3 to 12 ml/min.

Also, in the chlorophyll extraction step, the temperature of the complex supercritical extraction may be 30 to 70° C., preferably 40 to 60° C., and more preferably 45 to 55° C.

Also, in the chlorophyll extraction step, the pressure of the complex supercritical extraction may be 70 to 650 bar, preferably 100 to 500 bar, and more preferably 150 to 400 bar.

Also, in the chlorophyll extraction step, the duration of the complex supercritical extraction may be 45 to 300 minutes, preferably 60 to 250 minutes, and more preferably 70 to 220 minutes.

Also, the method for preparing chlorophyll-containing extract of the present invention may further include, before the chlorophyll extraction step, an impurity removal step of performing simple supercritical extraction on a plant or a microorganism.

Also, in the impurity removal step, the solvent of the simple supercritical extraction may be carbon dioxide.

Also, in the impurity removal step, the flow rate of the solvent of the simple supercritical extraction may be 20 to 120 mf/min, preferably 30 to 100 mf/min, and more preferably 40 to 85 mf/min.

Also, in the impurity removal step, the temperature of the simple supercritical extraction may be 30 to 70° C., preferably 40 to 60° C., and more preferably 45 to 55° C.

Also, in the impurity removal step, the pressure of the simple supercritical extraction may be 70 to 650 bar, preferably 100 to 500 bar, and more preferably 150 to 400 bar.

Also, in the impurity removal step, the duration of the simple supercritical extraction may be 30 to 350 minutes, preferably 40 to 300 minutes, and more preferably 50 to 250 minutes.

Also, the method for preparing a chlorophyll-containing extract of the present invention may further include, before the impurity removal step, a pre-treatment step of mixing a plant or a microorganism with oil.

Also, the oil of the pre-treatment step may be vegetable oil.

Also, the oil of the pre-treatment step may be seed oil, preferably selected from the group consisting of soybean oil, canola oil, sunflower seed oil, macadamia oil, peanut oil, grapeseed oil, pumpkin seed oil, flaxseed oil, linseed oil, olive oil, corn oil, safflower oil, sesame oil, almond oil, peach seed oil, apricot seed oil, walnut oil, rapeseed oil, raspberry oil, bilberry seed oil, cranberry seed oil, pomegranate seed oil, sacha inchi oil, fruit seed oil, sea buckthorn seed oil, chia oil, perilla oil; conjugated linolenic acid; diacylglycerol oil; omega 3 fatty acid, or a mixture thereof.

Also, in the pre-treatment step, the weight ratio of the oil to 100 parts by weight of the plant or the microorganism may be 1 to 50 parts by weight, preferably 2 to 10 parts by weight.

Also, the method for preparing a chlorophyll-containing extract of the present invention may further include, before the pre-treatment step, a powdering step of freeze-drying and then pulverizing a plant or a microorganism.

Also, an operating temperature coefficient may be 0.7 to 1.15, preferably 0.75 to 1.1, and more preferably 0.9 to 0.97.

A chlorophyll storage method for the present invention, in which chlorophyll is dissolved in oil having an unsaturated lipid structure and stored allows the structure of chlorophyll to be stably kept even for long-term storage. In particular, when chlorophyll is dissolved in squalene, chlorophyll was confirmed to remain even after 10 months or more. The storage period was found to be longer at lower storage temperature and with greater light blocking. The chlorophyll storage method for the present invention provides benefits such as long-term stability and useful applicability in food and other areas.

A chlorophyll-containing extract prepared through a complex supercritical fluid extraction process of the present invention has no organic solvent introduced during a preparation process, and thus, may be applied directly to food or medicine without any additional post-treatment. Also, an organic solvent removal process is not needed, and thus, there is an effect of saving installation cost and operation cost required therefor. In addition, since raw materials are extracted using only the carbon dioxide before the complex supercritical fluid extraction process in which ethanol is added, impurities in the raw materials may be effectively removed. Furthermore, the method for preparing a chlorophyll-containing extract of the present invention has an advantage of further increasing the content of chlorophyll in the chlorophyll-containing extract by performing pre-treatment on raw materials with oil when removing the impurities.

BRIEF DESCRIPTION OF THE DRAWINGS

FIG. 6 is a table and a graph showing storage stability test results for chlorophyll a powder added to squalene;

FIG. 7 is a table and a graph showing storage stability test results for chlorophyll a powder added to soybean oil;

FIG. 8 is a table and a graph showing storage stability test results for chlorophyll a powder added to canola oil;

FIG. 10 is a table and a graph showing storage stability test results for chlorophyll a powder added to grapeseed oil;

DETAILED DESCRIPTION

Figure 1:
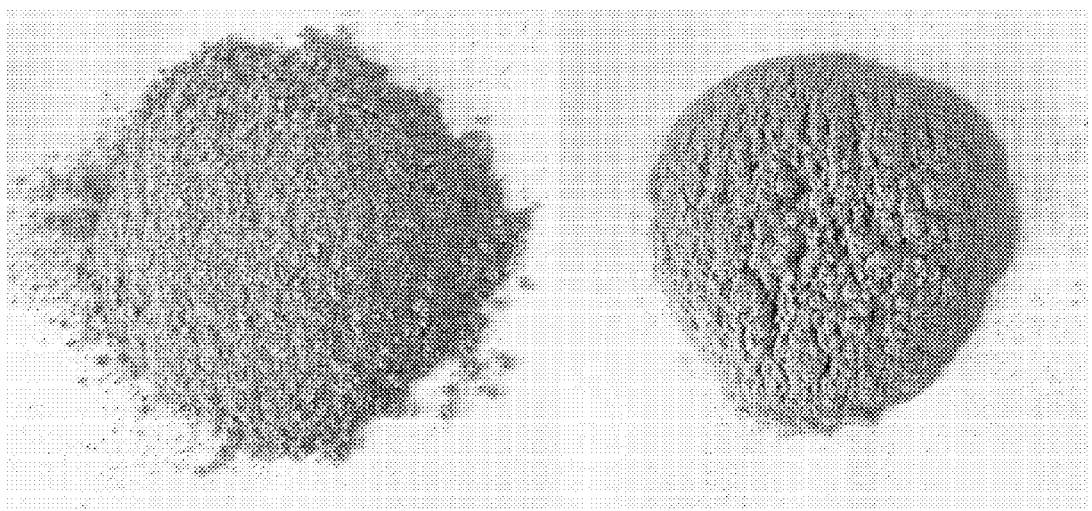
FIG. 1 is a photograph of wheatgrass powder before (A) and after (B) the chlorophyll extraction step of the present invention.

Hereinafter, preferred embodiments of the present invention will be described in detail.

However, below is only to describe specific embodiments in detail. The present invention may be changed in various ways and may have a number of forms, and thus, the present invention is not limited to specific embodiments illustrated. It is to be understood that the present invention includes all changes, equivalents, and alternatives falling within the spirit and scope of the present invention.

In addition, in the following description, many specific details such as specific components are described. However, they are only provided to aid in further understanding of the present invention, and thus, it will be apparent to those skilled in the art that the present invention may be practiced without these specific details. Also, in describing the present invention, detailed descriptions of related known functions or configurations will be omitted when it is determined that the detailed descriptions may unnecessarily obscure the gist of the present invention.

Also, the terms used in the present application are only used to describe specific embodiments, and are not intended to limit the present invention. Unless defined otherwise, all the terms used herein, including technical or scientific terms, may have the same meanings as those commonly understood by those skilled in the art to which the present invention pertains. Terms that are defined in a commonly used dictionary should be construed as having meanings consistent with the meanings in the context of the related art, and should meaning not be construed as having an ideal or overly formal meaning unless explicitly defined in the present application.

In the present application, the terms of a singular form may include a plural form unless the context clearly indicates otherwise.

In the present application, terms such as 'include,' 'contain,' or 'have' are intended to refer to the presence of features, components (or elements), and the like described in the specification, and do not imply that one or more other features or components are not present or cannot be added.

In the present application, the stabilization index is defined as follows (storage temperature units are absolute temperature K):

Stabilization index=100×(Final mass of chlorophyll/
Initial mass of chlorophyll)×Storage temperature In the present application, the operating temperature coefficient is defined as follows (all temperature units are absolute temperature K):

Operating temperature coefficient=(Freeze-drying temperature/Boiling point of co-solvent in chlorophyll extraction step)×(Boiling point of oil (low point of) in pre-treatment step/Critical temperature of solvent in impurity removal step).

The chlorophyll storage method includes a chlorophyll dissolving step of allowing chlorophyll to be included in oil having an unsaturated lipid structure.

The oil having an unsaturated lipid structure may be selected from the group consisting of docosahexaenoic acid (DHA), eicosapentaenoic acid (EPA), squalene, soybean oil, canola oil, sunflower seed oil, macadamia oil, peanut oil, grapeseed oil, pumpkin seed oil, flaxseed oil, linseed oil, olive oil, corn oil, safflower oil, sesame oil, pine-nut oil, conjugated linolenic acid, almond oil, peach seed oil, apricot seed oil, walnut oil, rapeseed oil, raspberry oil, bilberry seed oil, cranberry seed oil, pomegranate seed oil, sacha inchi oil, and other fruit seed oils, sea buckthorn oil, chia oil, perilla oil, diacylglycerol (DAG) oil, plant-derived sources of omega 3, fermentation sources of eicosapentaenoic acid (EPA), fermentation sources of docosahexaenoic acid (DHA), fermentation sources of other omega 3, 6, 9 oil combinations including fish oil and krill oil, sources of gamma linolenic acid (GLA) and/or stearidonic acid (SA), coconut oil, and a combination thereof, and particularly, squalene is preferred.

In particular, sources of DHA, EPA, or GLA above may be selected from the group consisting of fish oil, microorganisms, single cell sources, and vegetable oils, the microorganisms may be yeast, and the vegetable oils may be selected from the group consisting of flaxseed oil, soybean oil, canola oil, evening primrose oil, blackcurrant seed oil, borage oil, and echium oil.

The chlorophyll dissolving step may include the steps of:
(A) distilling a chlorophyll extract under reduced pressure to remove a solvent and solidify chlorophyll, and
(B) dissolving the solidified chlorophyll in oil having an unsaturated lipid structure, or include
(C) adding the oil containing an unsaturated lipid structure to the chlorophyll extract to prepare a mixture, and
(D) separating layers of the mixture to perform fractional extraction.

Here, the solidified chlorophyll or the chlorophyll extract may be obtained through a chlorophyll-containing extract preparation method including a chlorophyll extraction step below of performing complex supercritical extraction on plants or microorganisms containing chlorophyll.

A method for increasing the stability of chlorophyll according to the present invention to achieve the above object uses oil having an unsaturated structure with double bonds in order to effectively prevent the step of transferring energy to neighboring chlorophyll when chlorophyll excited due to an impact from light energy or temperature releases energy, and to offset the energy with the molecular rotational motion and vibrational motion of a stabilizer.

The oil containing used in the above case may be docosahexaenoic acid (DHA), eicosapentaenoic acid (EPA), and squalene, and other oils that are applicable may be soybean oil, canola oil, sunflower seed oil, macadamia oil, peanut oil, grapeseed oil, pumpkin seed oil, flaxseed oil, linseed oil, olive oil, corn oil, safflower oil, sesame oil, pine-nut oil, conjugated linolenic acid, almond oil, peach seed oil, apricot seed oil, walnut oil, rapeseed oil, raspberry oil, bilberry seed oil, cranberry seed oil, pomegranate seed oil, sacha inchi oil, and other fruit seed oils, sea buckthorn oil, chia oil, perilla oil, diacylglycerol (DAG) oil, plant-derived sources of omega 3, fermentation sources of eicosapentaenoic acid (EPA), fermentation sources of docosahexaenoic acid (DHA), fermentation sources of other omega 3, 6, 9 oil combinations including fish oil and krill oil, sources of gamma linolenic acid (GLA) and/or stearidonic acid (SA), fractionated coconut oil, and a combination thereof, but are not limited thereto. Sources of DHA, EPA and GLA include fish oil, yeast or other microorganisms or single cell sources and vegetable oils, mainly flaxseed, soybean, and canola, but are not limited thereto. Sources of GLA may be evening primrose oil, blackcurrant seed oil, borage oil, and echium oil, but are not limited thereto.

The method for dissolving the extracted chlorophyll in oil may include a method for removing a solvent through distillation under reduced pressure after extraction, and then directly dissolving the solidified chlorophyll in the selected oil, or a method for separating layers by adding the oil to alcohol, etc. containing the extract, and then performing fractional extraction, but is not limited thereto.

Observation of chlorophyll decomposition after storing the chlorophyll extracted in the oil showed that when chlorophyll was dissolved in squalene, chlorophyll remained for more than 10 months, and lower temperature and greater light blocking make it easier for chlorophyll to remain.

Accordingly, in the chlorophyll storage method of the present invention, the chlorophyll dissolved in oil may be stored in a dark place at −100 to 12° C., −90 to 8° C., or −80 to 5° C. after the chlorophyll dissolving step. When the storage temperature is lower than the above ranges, as a downside, the operating cost required for cooling excessively rises, whereas when the storage temperature is higher than the above ranges, as a downside, the amount of destroyed chlorophyll increases.

In the present application, in particular, a new parameter called stabilization index was introduced to select oil used for storage of chlorophyll, and the stabilization index is defined as follows (storage temperature units are absolute temperature K):

Stabilization index=100×(Final mass of chlorophyll/
Initial mass of chlorophyll)×Storage temperature Various experiments indicated that it is desirable to select oil having a stabilization index of 15000 to 25315, 17000 to 25310, or 18500 to 25305. When the stabilization index is less than the above ranges, chlorophyll is excessively destroyed over time, whereas when the stabilization index is greater than the above ranges, it is physically extremely difficult as well as economic feasibility sharply decreases.

Through the above method, chlorophyll may be stored with long-term stability, and may be usefully applied in food and other areas.

Meanwhile, a chlorophyll extract used in the chlorophyll storage method of the present invention may be obtained through a chlorophyll-containing extract preparation method including a chlorophyll extraction step of performing complex supercritical extraction on plants or microorganisms containing chlorophyll. Here, complex supercritical extraction refers to performing extraction in combination of a co-solvent with a main solvent, instead of using the main solvent alone.

The plant or the microorganism used as a raw material for extraction is not limited as long as it is a plant or a microorganism including chlorophyll a, chlorophyll b, chlorophyll c1, chlorophyll c2, chlorophyll d, chlorophyll f, bacteriochlorophyll, or a mixture thereof. For example, the plant or the microorganism may be selected from the group consisting of woody leaves, woody buds, herbal stems, herbal leaves, herbal buds; cyanophyta, prochlorophyta, rhodophyta, chlorophyta, heterokontophyta, tribophyta, glaucophyta, chlorarachniophytes, euglenophyta, euglenoids, haptophyta, chrysophyta, cryptophyta, cryptomonads, dinophyta, dinoflagellata, pyrmnesiophyta, bacillariophyta, xanthophyta, eustigmatophyta, raphidophyta, phaeophyta, phytoplankton; blue-green bacteria such as *spirulina*; microalgae such as chlorella genus, *scenedesmus* genus, *dunaliella* genus, *chlamydomonas* genus, *haematococcus* genus, and *botryococcus* genus; and a combination thereof.

In the chlorophyll extraction step, a main solvent may be carbon dioxide, and a co-solvent may be ethanol.

In the chlorophyll extraction step, the total flow rate of the complex supercritical extraction may be 20 to 120 mf/min, preferably 30 to 100 mf/min, and more preferably 40 to 85 mf/min. When the total flow rate is less than the above range, there is a problem in that extraction duration becomes longer. On the contrary, when exceeding the above range, the extraction duration becomes shorter, but there is a problem in that a supercritical state may not be maintained during the process.

In the chlorophyll extraction step, the flow rate of the co-solvent of the complex supercritical extraction may be 1 to 20 mf/min, preferably 2 to 15 mf/min, and more preferably 3 to 12 mf/min. When the flow rate of the co-solvent is less than the above range, there is a problem in that extraction duration becomes longer. On the contrary, when exceeding the above range, the extraction duration becomes shorter, but there is a problem in that a supercritical state may not be maintained during the process.

In the chlorophyll extraction step, the temperature of the complex supercritical extraction may be 30 to 70° C., preferably 40 to 60° C., and more preferably 45 to 55° C. When the temperature of the complex supercritical extraction is less than the above range, there is a problem in that the chlorophyll extraction efficiency decreases. On the contrary, when exceeding the above range, there is a problem in that impurities are extracted together.

In the chlorophyll extraction step, the pressure of the complex supercritical extraction may be 70 to 650 bar, preferably 100 to 500 bar, and more preferably 150 to 400 bar. When the pressure of the complex supercritical extraction is less than the above range, there is a problem in that the chlorophyll extraction efficiency decreases. On the contrary, when exceeding the above range, there is a problem in that impurities are extracted together.

In the chlorophyll extraction step, the duration of the complex supercritical extraction may be 45 to 300 minutes, preferably 60 to 250 minutes, and more preferably 70 to 220 minutes. When the duration of the complex supercritical extraction is less than the above range, there is a problem in that chlorophyll is not completely extracted so that some chlorophyll remains in raw materials. On the contrary, when exceeding the above range, since all chlorophyll is already extracted, there is no chlorophyll left to be extracted in a later stage of the extraction, so that there is a problem in that economic feasibility decreases.

The method for preparing a chlorophyll-containing extract of the present invention may further include, before the chlorophyll extraction step, an impurity removal step of performing simple supercritical extraction on a plant or a microorganism. Here, the simple supercritical extraction refers to extracting using a main solvent alone. It is the main feature of the present invention that impurities are extracted first using the main solvent alone as described above before extracting chlorophyll in combination of the main solvent and a co-solvent.

In the impurity removal step, the solvent of the simple supercritical extraction may be carbon dioxide.

In the impurity removal step, the flow rate of the solvent of the simple supercritical extraction may be 20 to 120 mf/min, preferably 30 to 100 mf/min, and more preferably 40 to 85 mf/min. When the flow rate of the co-solvent of the simple supercritical extraction is less than the above range, there is a problem in that extraction duration becomes longer. On the contrary, when exceeding the above range, the extraction duration becomes shorter, but there is a problem in that a supercritical state may not be maintained during the process.

In the impurity removal step, the temperature of the simple supercritical extraction may be 30 to 70° C., preferably 40 to 60° C., and more preferably 45 to 55° C. When the temperature of the simple supercritical extraction is less than the above range, there is a problem in that impurities are not completely removed. On the contrary, when exceeding the above range, there is a problem in that some of chlorophyll is removed together with the impurities.

In the impurity removal step, the pressure of the simple supercritical extraction may be 70 to 650 bar, preferably 100 to 500 bar, and more preferably 150 to 400 bar. When the pressure of the simple supercritical extraction is less than the above range, there is a problem in that impurities are not completely removed. On the contrary, when exceeding the above range, there is a problem in that some of chlorophyll is removed together with the impurities.

In the impurity removal step, the duration of the simple supercritical extraction may be 30 to 350 minutes, preferably 40 to 300 minutes, and more preferably 50 to 250 minutes. When the duration of the simple supercritical extraction is less than the above range, there is a problem in that impurities are not completely extracted so that some impurities remain in raw materials. On the contrary, when exceeding the above range, since all impurities are already extracted, there are no impurities left to be extracted in a later stage of the extraction, so that there is a problem in that economic feasibility decreases and some chlorophyll is removed.

The method for preparing a chlorophyll-containing extract of the present invention may further include, before the impurity removal step, a pre-treatment step of mixing a plant or a microorganism with oil. When raw material powder is mixed with oil, impurities in raw materials are dissolved in the oil. As a result, the efficiency of removing impurities in the raw materials is significantly increased in the impurity removal step, and this pre-treatment step constitutes another major feature of the present invention.

The oil of the pre-treatment step may be vegetable oil.

The oil of the pre-treatment step may be seed oil, preferably selected from the group consisting of soybean oil, canola oil, sunflower seed oil, macadamia oil, peanut oil, grapeseed oil, pumpkin seed oil, flaxseed oil, linseed oil, olive oil, corn oil, safflower oil, sesame oil, almond oil, peach seed oil, apricot seed oil, walnut oil, rapeseed oil, raspberry oil, bilberry seed oil, cranberry seed oil, pomegranate seed oil, sacha inchi oil, fruit seed oil, sea buckthorn seed oil, chia oil, perilla oil; conjugated linolenic acid; diacylglycerol oil; omega 3 fatty acid, or a mixture thereof.

In the pre-treatment step, the weight ratio of the oil to 100 parts by weight of the plant or the microorganism may be 1 to 50 parts by weight, preferably 2 to 10 parts by weight. When the weight ratio of the oil to the raw materials is less than the above range, there is a problem in that impurities are not completely removed. On the contrary, when exceeding the above range, there is a problem in that some of chlorophyll is removed together with the impurities.

The method for preparing a chlorophyll-containing extract of the present invention may further include, before the pre-treatment step, a powdering step of freeze-drying and then pulverizing a plant or a microorganism.

Since the present invention is operated under severe conditions other than room temperature and atmospheric pressure like supercritical extraction, it is necessary to design a process that prevents the operating cost from increasing rapidly. Among the above, processing temperatures, which are important, may include the freeze-drying temperature, the boiling point of the co-solvent in the chlorophyll extraction step, the boiling point of the oil in the pre-treatment step, and the critical temperature of the solvent in the impurity removal step. Among the above, the higher the freeze-drying temperature, the lower the operating cost. The lower the boiling point of the co-solvent in the chlorophyll extraction step, the lower the operating cost. The higher the boiling point of the oil in the pre-treatment step, the easier the mixing with the raw material powder. The lower the critical temperature of the solvent in the impurity removal step, the lower the operating cost.

With this concept in mind, the present invention has introduced a new operating variable called the operating temperature coefficient, and the operating temperature coefficient is defined as follows (all temperature units are absolute temperature K):

Operating temperature coefficient=(Freeze-drying temperature/Boiling point of co-solvent in chlorophyll extraction step)×(Boiling point of oil (low point of) in pre-treatment step/Critical temperature of solvent in impurity removal step).

After reviewing various materials, it has been found that an operating temperature coefficient may be 0.7 to 1.15, preferably 0.75 to 1.1, and more preferably 0.9 to 0.97. When the operating temperature coefficient is less than the above range, there is a disadvantage in that the operating cost increases excessively. On the contrary, when exceeding the above range, the operating cost decreases, but there is a problem in that the material cost increases due to the use of expensive materials.

Using chlorophyll obtained through the above method, it was possible to obtain a variety of chlorophyll derivatives derived from the chlorophyll through a method known in the art.

Hereinafter, examples of the present invention will be described in detail. However, the following examples are illustrative of the present invention, and the present invention is not limited by the following examples.

Examples

Experimental Example: Measuring Mass of Chlorophyll a

In order to analyze the content of extracted chlorophyll, high-performance liquid chromatography (AGILENT, USA) was used, and the column used was Shimadzu Shimpack C18 analytical column (250 mm×4.6 mm, 5 μm, 100). The peak was detected as ultraviolet ray absorption using a diode array detector. The injection volume was 20 μg, and the flow rate was 1 ml/min. The reference material for chlorophyll a was purchased from Aldrich Chemical Co. (Milwaukee, Wis.), and was used without a further purification process.

Comparative Example 1: Alcohol Extraction Step 1 g of freeze-dried wheatgrass powder (Dreams, South Korea) was added to 25 mf of ethanol (98%), stirred for 2 hours at room temperature to be extracted, and then filtered using a filter paper. Thereafter, the filtrate was analyzed according to Test Example above to obtain the content of chlorophyll a. According to the analysis result, the amount of chlorophyll a was 3.8 mg, and the mass of total solids remaining after ethanol was removed by vacuum distillation was confirmed to be 165 mg.

Example 1: Supercritical Extraction Step 50 g of freeze-dried wheatgrass powder (Dreams, South Korea) was extracted for 60 minutes under the conditions of 350 bar, 50° C., and a supercritical carbon dioxide flow rate of 60 ml/min to remove impurities, and then re-extracted for 120 minutes under the conditions of 350 bar, 50° C., a supercritical carbon dioxide flow rate of 60 mf/min, and a co-solvent ethanol flow rate of 5 ml/min to analyze the content of chlorophyll a. According to the analysis result, the amount of chlorophyll a was 235 mg, and the mass of total solids remaining after ethanol was removed by vacuum distillation was confirmed to be 4250 mg.

Preparation Example 1: Pre-Treatment Step+Impurity Removal Step 50 g of freeze-dried wheatgrass powder (Dreams, South Korea) and 2.5 g of grapeseed oil as shown in (A) of FIG. 1 were mixed well with a mixer to be prepared. The prepared mixture of wheatgrass and grapeseed oil was extracted for 120 minutes under the conditions of 350 bar, 50° C., and a supercritical carbon dioxide flow rate of 60 mf/min to obtain wheatgrass powder with improved clarity of green color by removing impurities as shown in (B) of FIG. 1.

Comparative Example 2: Preparation Example 1+Comparative Example 1

The content of chlorophyll a obtained through the step of Comparative Example 1 was analyzed with respect to the wheatgrass powder obtained through the steps of Preparation Example 1. According to the analysis result, the amount of chlorophyll a was 4.2 mg, and the mass of total solids remaining after ethanol was removed by vacuum distillation was confirmed to be 87.5 mg.

Example 2: Preparation Example 1+Example 1

The content of chlorophyll a obtained through the step of Example 1 was analyzed with respect to the wheatgrass powder obtained through the steps of Preparation Example 1. According to the analysis result, the amount of chlorophyll a was 240 mg, and the mass of total solids remaining after ethanol was removed by vacuum distillation was confirmed to be 3116 mg.

The result of converting the amount of chlorophyll a analyzed in each of Comparative Examples 1 and 2 and Examples 1 and 2 with respect to 1 g of dry wheatgrass powder and the extraction efficiency (=mass of chlorophyll a/mass of total solids) are shown in Table 1 below. Also, the results of high-performance liquid chromatography of each thereof are shown in FIG. 2.

TABLE 1

| Wheatgrass powder | Comparative Example 1 | Example 1 | Comparative Example 2 | Example 2 |
|---|---|---|---|---|
| Chlorophyll (mg) | 3.8 | 4.7 | 4.2 | 4.8 |
| Extraction efficiency (%) | 2.3 | 5.5 | 4.8 | 7.2 |

Figure 2:
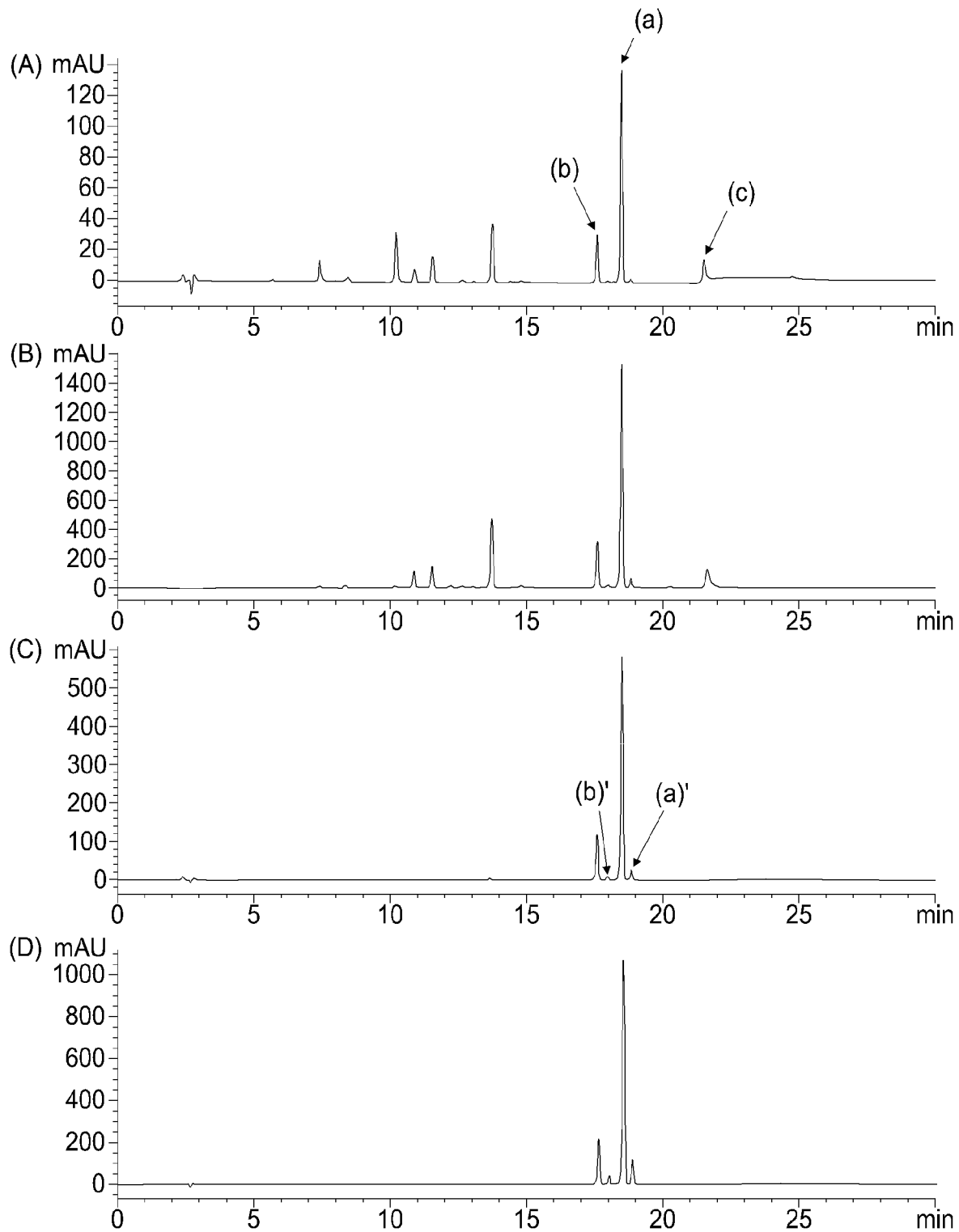
FIG. 2 is an HPLC result for analyzing the content of chlorophyll in an extract after the supercritical extraction of wheatgrass powder {(A) Comparative Example 1, (B) Example 1, (C) Comparative Example 2, (D) Example 2 [(a) chlorophyll a, (a') chlorophyll a epimer, (b) chlorophyll b, (b') chlorophyll b epimer, (c) carotenoid]}.

According to FIG. 2 above, a characteristic peak of chlorophyll b and a characteristic peak of chlorophyll a were observed in the 17 minute and 18 minute, respectively, and in addition, a characteristic peak of carotenoid was observed in the 22 minute.

In the drawing of Comparative Example 1 ((A) of FIG. 2), various impurity peaks were observed before the 15 minute, and in the drawing of Example 1 ((B) of FIG. 2), it was confirmed that some impurities were removed.

In the case of Comparative Example 2 ((C) of FIG. 2) and Example 2 ((D) of FIG. 2), it was confirmed that most of the impurities were removed. However, after the removal of the impurities, it was confirmed that the chlorophyll content and extraction efficiency of supercritical extraction in which a co-solvent was used were better than those of alcohol extraction.

Comparative Examples 3 and 4, and Example 3 and 4: Barley Sprout Powder

The same procedures as in Comparative Examples 1 and 2 and Examples 1 and 2 were performed, but instead of wheatgrass powder, barley sprout powder (Dreams, South Korea) was used. The result of converting the analyzed amount of chlorophyll a with respect to 1 g of dry barley sprout powder and the extraction efficiency (=mass of chlorophyll a/mass of total solids) are shown in Table 2 below.

TABLE 2

| Barley sprout powder | Comparative Example 3 | Example 3 | Comparative Example 4 | Example 4 |
|---|---|---|---|---|
| Chlorophyll (mg) | 3.75 | 4.3 | 4.1 | 4.7 |
| Extraction efficiency (%) | 2.5 | 4 | 3.2 | 6 |

Comparative Examples 5 and 6, and Example 5 and 6: *Spirulina* Powder

The same procedures as in Comparative Examples 1 and 2 and Examples 1 and 2 were performed, but instead of wheatgrass powder, *spirulina* powder (NutriVita Shop, USA) was used. The result of converting the analyzed amount of chlorophyll a with respect to 1 g of dry *spirulina* powder and the extraction efficiency (=mass of chlorophyll a/mass of total solids) are shown in Table 3 below.

TABLE 3

| Spirulina powder | Comparative Example 5 | Example 5 | Comparative Example 6 | Example 6 |
|---|---|---|---|---|
| Chlorophyll (mg) | 2.8 | 3.2 | 2.8 | 4 |
| Extraction efficiency (%) | 1.9 | 3.5 | 3.1 | 4.7 |

Example 7: Storage Method with Excellent Stability

In order to analyze the content of extracted chlorophyll, high-performance liquid chromatography (HPLC) was used. Purification was performed using the Agilent 1100 Series HPLC system from AGILENT, and the column used was Shimadzu Shim-pack C18 analytical column (250 mm×4.6 mm, 5 μm, 100). The peak was detected as ultraviolet ray absorption using a diode array detector. The injection volume was 20 jig, and the flow rate was 1 mf/min.

Figure 3:
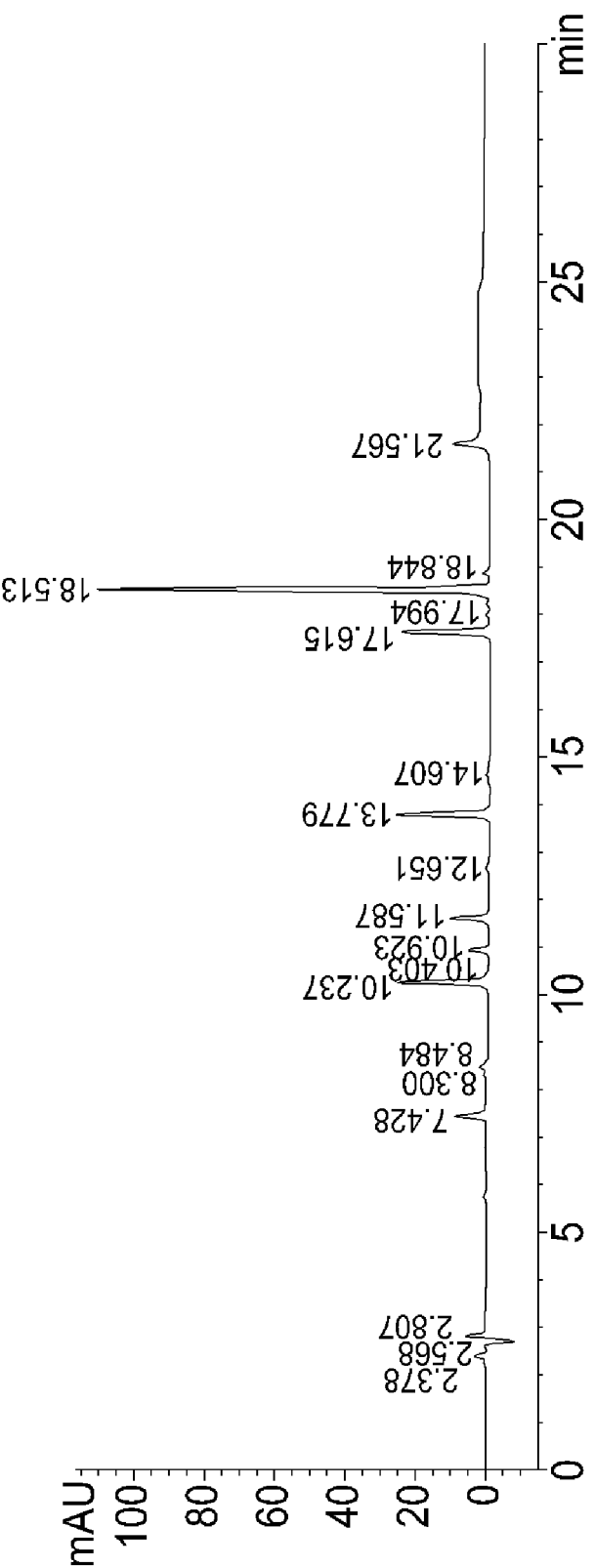
FIG. 3 is an HPLC graph of chlorophyll extracted in ethanol from freeze-dried wheatgrass powder.
Figure 4:
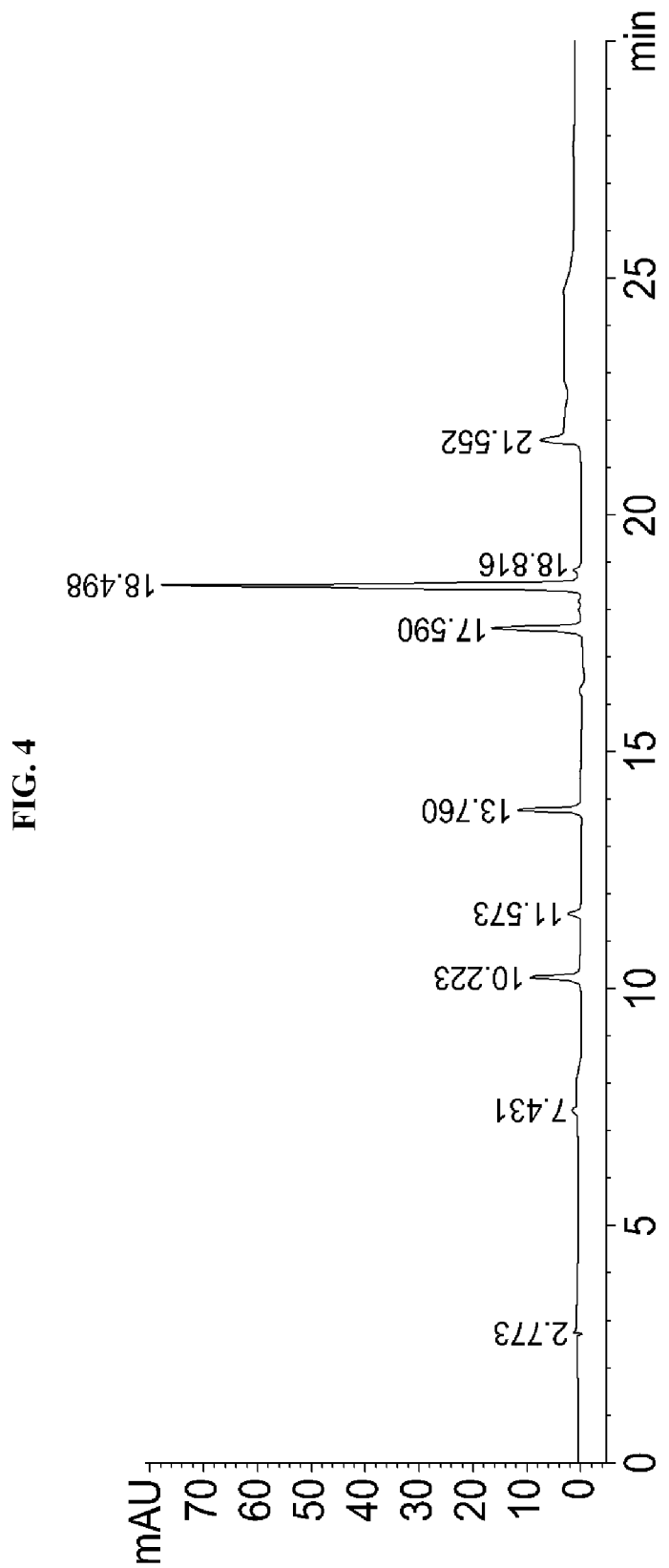
FIG. 4 is an HPLC graph in which chlorophyll extracted in ethanol of FIG. 3 is re-extracted with squalene.

A solvent to be separated was separated using a gradation method as shown in the table below. The reference material for chlorophyll a was purchased from Aldrich Chemical Co. (Milwaukee, Wis.), and was used without a further purification process. In FIGS. 2 to 4, peaks corresponding to retention time of about 18.5 minute refer to chlorophyll a.

TABLE 4

| Time | MeOH 80% + 0.5M NH$_4$Ac 20% | ACN 90% + water 10% | Ea |
|---|---|---|---|
| 0 | 100% | | |
| 4 | | 100% | |
| 18 | | 20% | 80% |
| 21 | | 100% | |
| 24 | 100% | | |

Extraction of Chlorophyll a

Substances for extracting chlorophyll a include young wheatgrass, young barley sprout, and young rice sprout including *spirulina* and chlorella.

Organic solvents that may be used in the present invention include various organic solvents known in the art. For example, (1) C1-4 anhydrous or hydrous lower alcohol (methanol, ethanol, propanol, butanol, etc.), (2) a mixed solvent of the lower alcohol and water, (3) acetone, (4) ethyl acetate, (5) chloroform, (6) butyl acetate, (7) 1,3-butylene glycol, (8) hexane, and (9) diethyl ether may be used as organic solvents. Preferably, methanol or ethanol may be used, and more preferably, ethanol may be used.

1 g of freeze-dried wheatgrass powder was immersed in 25 ml of ethanol (98%), stirred for 2 hours, and filtered using a filter paper, and then the volume of the filtered ethanol was controlled to be 50 ml. The HPLC graph of chlorophyll extracted through the above method is shown in FIG. 3.

50 ml of squalene was added to the extracted ethanol (50 ml), and the mixture was stirred vigorously, and then layers were separated for 2 minutes, and the HPLC graph showing measurement of the squalene layer taken therefrom is shown in FIG. 4. It was observed that the peak 10 minutes before the retention time disappeared, and it was confirmed that more than about 80% of chlorophyll a moved to the squalene layer.

Figure 5:
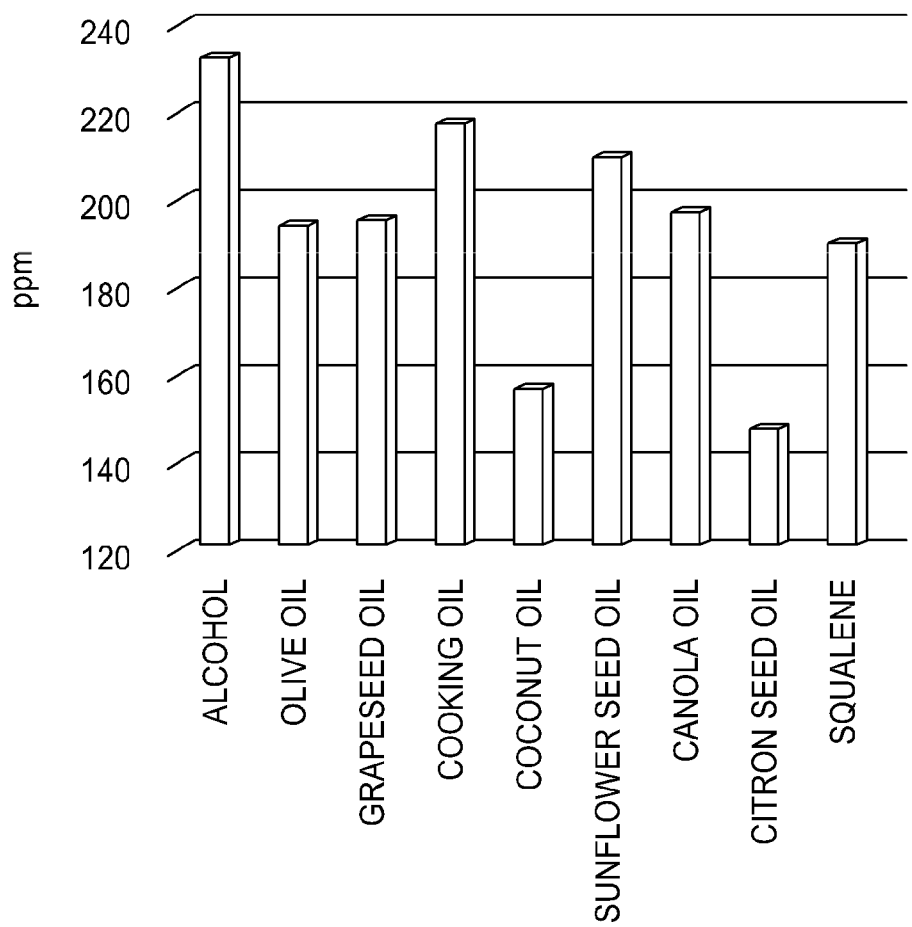
FIG. 5 is an HPLC graph using soybean oil, canola oil, sunflower seed oil, grapeseed oil, olive oil, and coconut oil instead of squalene of FIG. 4 and a graph showing extraction efficiency.
Figure 9:
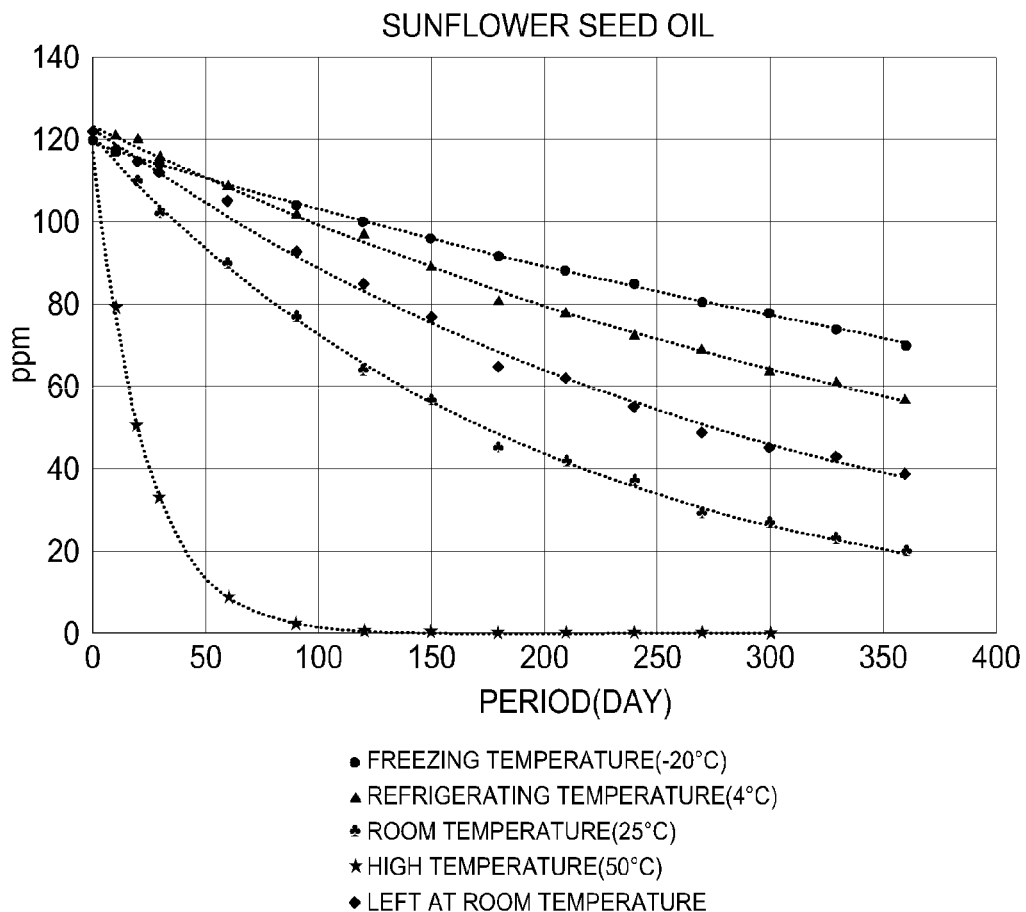
FIG. 9 is a table and a graph showing storage stability test results for chlorophyll a powder added to sunflower seed oil.
Figure 11:
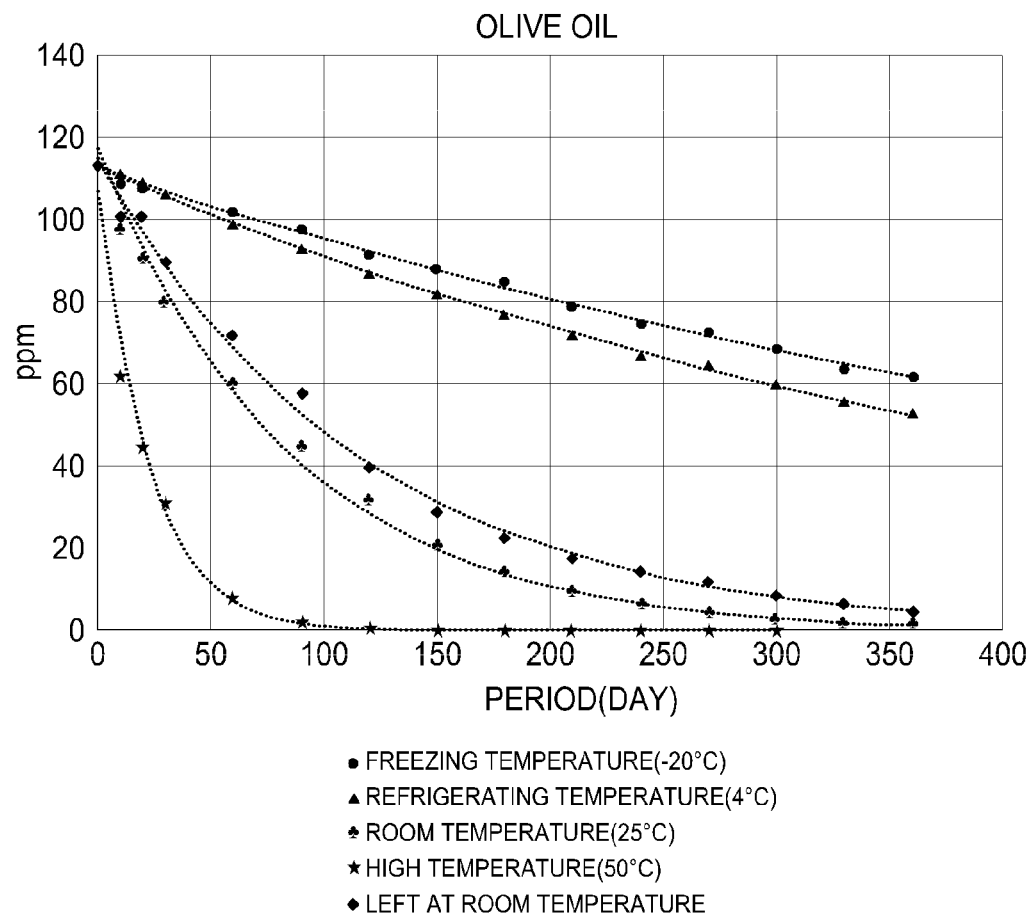
FIG. 11 is a table and a graph showing storage stability test results for chlorophyll a powder added to olive oil.
Figure 12:
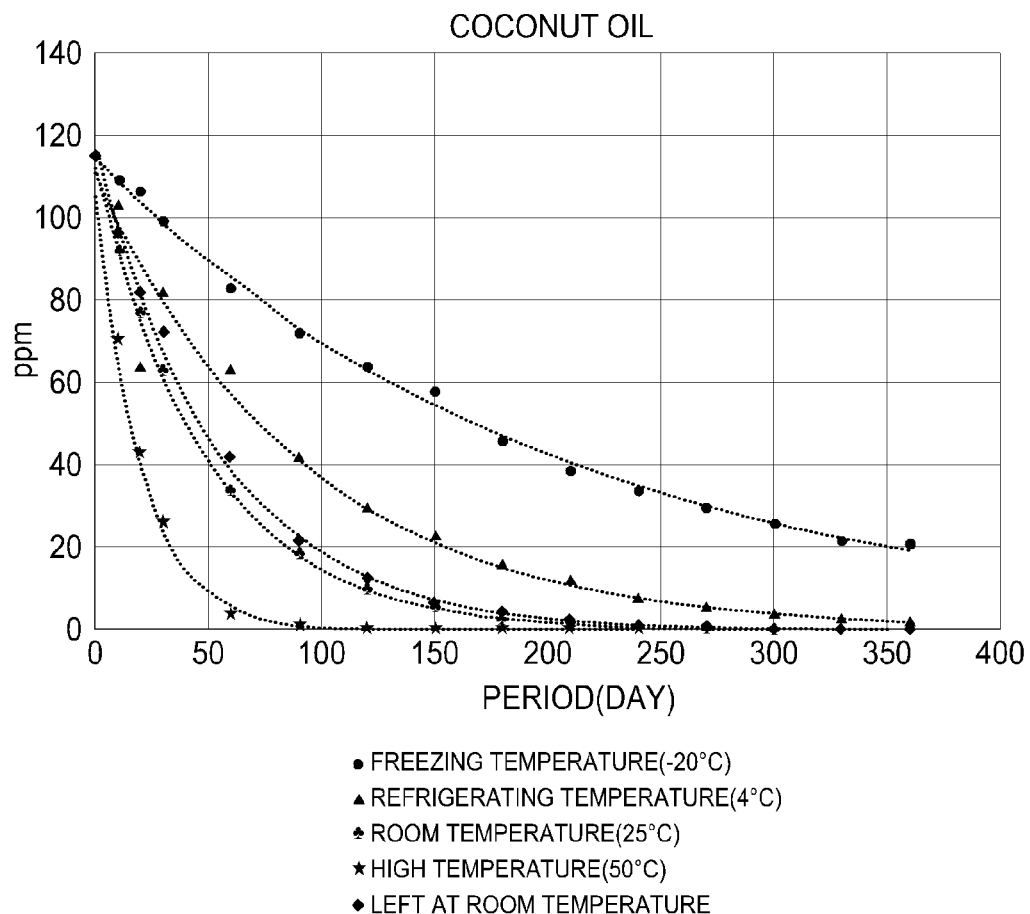
FIG. 12 is a table and a graph showing storage stability test results for chlorophyll a powder added to coconut oil.

Based on results of additional experiments using soybean oil, canola oil, sunflower seed oil, grapeseed oil, olive oil, coconut oil, etc., which may be used as stabilizers, it was confirmed from FIG. 5 that 93%, 85%, 90%, 84%, 83%, and 67% of chlorophyll a were respectively dissolved in each oil phase.

Chlorophyll Stability

The storage stability of chlorophyll a stabilization candidate materials used in the above process for chlorophyll-a was tested. Samples were collected for each storage period at various temperatures, and the content of chlorophyll a was analyzed using the HPLC system described above.

Temperatures for the test were respectively freezing temperature (−20° C.), refrigerating temperature (4° C.), room temperature (25° C.), high temperature (50° C.), and being left at room temperature.

The chlorophyll a stabilization candidate materials (squalene, soybean oil, canola oil, sunflower seed oil, grapeseed oil, olive oil, coconut oil) and the filtered chlorophyll a ethanol extract were mixed in a volume ratio of 1:1, and the mixture was stirred vigorously, and then separated into layers for 2 minutes to obtain an oil layer from the separation. In this process, ethanol was removed. Thereafter, the obtained was stored for a predetermined period in a dark place for each temperature to collect samples for each storage period, and then the content of chlorophyll a was analyzed using the HPLC system described above.

Results of the storage stability test on chlorophyll a powder added to oil as a stabilizer showed that chlorophyll a added to various oils that may be used as food materials was stabilized for a considerable period of time, and half-life of chlorophyll a in squalene, soybean oil, canola oil, sunflower seed oil, grapeseed oil, olive oil, and coconut oil increased significantly to 7 months, 2.5 months, 4 months, 6 months, 5 months, 3 months, and 1.5 months, respectively, at room temperature storage. FIGS. 6 to 12 show that the lower the storage temperature, the greater the half-life.

Although the preferred embodiments of the present invention have been described above, the present invention is not limited to the specific embodiments described above. Various modifications may be implemented by those skilled in the art without departing from the gist of the present invention. Therefore, the scope of the present invention should not be limited to the embodiments described above, but should be defined by the following claims as well as the equivalents thereof.

What is claimed is:

1. A method for storing chlorophyll, the method comprising:
    preparing chlorophyll to be stored; and
    dissolving the chlorophyll in oil having an unsaturated lipid structure to allow the chlorophyll to be included in the oil,
    wherein the preparation of the chlorophyll to be stored comprises:
        pretreating a plant containing the chlorophyll and/or a microorganism containing the chlorophyll by mixing the plant and/or the microorganism with oil selected from the group consisting of soybean oil, canola oil, sunflower seed oil, macadamia oil, peanut oil, grapeseed oil, pumpkin seed oil, flaxseed oil, linseed oil, olive oil, corn oil, safflower oil, sesame oil, almond oil, peach seed oil, apricot seed oil, walnut oil, rapeseed oil, raspberry oil, bilberry seed oil, cranberry seed oil, pomegranate seed oil, sacha inchi oil, sea buckthorn seed oil, chia oil, *perilla* oil, and a mixture thereof;
        removing an impurity by performing a first supercritical extraction on the plant and/or the microorganism with a solvent comprising carbon dioxide; and
        preparing a chlorophyll extract by performing a second supercritical extraction on the plant and/or the microorganism with a solvent comprising carbon dioxide as a main solvent and ethanol as a co-solvent; and
    wherein the dissolving of the chlorophyll in the oil comprises:
        distilling the chlorophyll extract under reduced pressure and solidifying the chlorophyll to obtain the chlorophyll to be stored; and
        dissolving the solidified chlorophyll in the oil selected from the group consisting of docosahexaenoic acid (DHA), eicosapentaenoic acid (EPA), squalene, soybean oil, canola oil, sunflower seed oil, macadamia oil, peanut oil, grapeseed oil, pumpkin seed oil, flaxseed oil, linseed oil, olive oil, corn oil, safflower oil, sesame oil, pine-nut oil, conjugated linolenic acid, almond oil, peach seed oil, apricot seed oil, walnut oil, rapeseed oil, raspberry oil, bilberry seed oil, cranberry seed oil, pomegranate seed oil, sacha inchi oil, sea buckthorn oil, chia oil, *perilla* oil, diacylglycerol oil, plant-derived sources of omega 3, fermentation sources of eicosapentaenoic acid (EPA), fermentation sources of docosahexaenoic acid (DHA), fish oil, krill oil, sources of gamma linolenic acid (GLA) and/or stearidonic acid (SA), coconut oil and a combination thereof.

2. The method of claim 1, wherein the oil having the unsaturated lipid structure is selected from the group consisting of docosahexaenoic acid (DHA), eicosapentaenoic acid (EPA), squalene, canola oil, macadamia oil, peanut oil, pumpkin seed oil, flaxseed oil, linseed oil, corn oil, safflower oil, sesame oil, pine-nut oil, almond oil, peach seed oil, apricot seed oil, rapeseed oil, raspberry oil, bilberry seed oil, cranberry seed oil, pomegranate seed oil, sacha inchi oil, sea buckthorn oil, chia oil, *perilla* oil, plant-derived sources of omega 3, fermentation sources of eicosapentaenoic acid (EPA), fermentation sources of docosahexaenoic acid (DHA), fish oil, krill oil, sources of gamma linolenic acid (GLA) and/or stearidonic acid (SA), coconut oil and a combination thereof.

3. The method of claim 1, wherein the unsaturated lipid structure is docosahexaenoic acid (DHA) or eicosapentaenoic acid (EPA), and a source of the DHA or the EPA is selected from the group consisting of fish oil, microorganisms, single cell sources, and a combination thereof.

4. The method of claim 1, wherein the unsaturated lipid structure is gamma linolenic acid (GLA), and a source of the GLA is selected from the group consisting of fish oil, microorganisms, single cell sources, and a combination thereof.

5. The method of claim 1, wherein a total flow rate of the first supercritical extraction is in the range of 20 to 120 ml/min;
    a flow rate of the co-solvent of the first supercritical extraction is in the range of 1 to 20 ml/min;
    a temperature of the first supercritical extraction is in the range of 30 to 70° C.;
    a pressure of the first supercritical extraction is in the range of 70 to 650 bar; and
    a duration of the first supercritical extraction is in the range of 30 to 350 minutes.

6. The method of claim 1, wherein a flow rate of the solvent of the first supercritical extraction is in the range of 20 to 120 ml/min;
    a temperature of the second supercritical extraction is in the range of 30 to 70° C.;
    a pressure of the second supercritical extraction is in the range of 70 to 650 bar; and a duration of the second supercritical extraction is in the range of 45 to 300 minutes.

7. The method of claim 1, wherein the oil is an isolated squalene.

8. A method for storing chlorophyll, the method comprising:
preparing chlorophyll to be stored; and
dissolving the chlorophyll in oil having an unsaturated lipid structure to allow the chlorophyll to be included in the oil,
wherein the preparation of the chlorophyll to be stored comprises:
pretreating a plant containing the chlorophyll and/or a microorganism containing the chlorophyll by mixing the plant and/or the microorganism with oil selected from the group consisting of soybean oil, canola oil, sunflower seed oil, macadamia oil, peanut oil, grapeseed oil, pumpkin seed oil, flaxseed oil, linseed oil, olive oil, corn oil, safflower oil, sesame oil, almond oil, peach seed oil, apricot seed oil, walnut oil, rapeseed oil, raspberry oil, bilberry seed oil, cranberry seed oil, pomegranate seed oil, sacha inchi oil, sea buckthorn seed oil, chia oil, *perilla* oil, and a mixture thereof;
removing an impurity by performing a first supercritical extraction on the plant and/or the microorganism with a solvent comprising carbon dioxide; and
preparing a chlorophyll extract by performing a second supercritical extraction on the plant and/or the microorganism with a solvent comprising carbon dioxide as a main solvent and ethanol as a co-solvent,
wherein the dissolving of the chlorophyll in the oil comprises:
mixing the prepared chlorophyll extract with the oil to prepare a mixture, the oil selected from the group consisting of docosahexaenoic acid (DHA), eicosapentaenoic acid (EPA), squalene, soybean oil, canola oil, sunflower oil, macadamia oil, peanut oil, grapeseed oil, pumpkin seed oil, flaxseed oil, linseed oil, olive oil, corn oil, safflower oil, sesame oil, pine-nut oil, conjugated linolenic acid, almond oil, peach seed oil, apricot seed oil, walnut oil, rapeseed oil, raspberry oil, bilberry seed oil, cranberry seed oil, pomegranate seed oil, sacha inchi oil, sea buckthorn oil, chia oil, *perilla* oil, diacylglycerol oil, plant-derived sources of omega 3, fermentation sources of eicosapentaenoic acid (EPA), fermentation sources of docosahexaenoic acid (DHA), fish oil, krill oil, sources of gamma linolenic acid (GLA) and/or stearidonic acid (SA), coconut oil and a combination thereof,
separating layers of the mixtures to perform fractional extraction.

9. The method of claim 8, wherein a total flow rate of the first supercritical extraction is in the range of 20 to 120 ml/min;
a flow rate of the co-solvent of the first supercritical extraction is in the range of 1 to 20 ml/min;
a temperature of the first supercritical extraction is in the range of 30 to 70° C.;
a pressure of the first supercritical extraction is in the range of 70 to 650 bar; and
a duration of the first supercritical extraction is in the range of 30 to 350 minutes.

10. The method of claim 8, wherein a flow rate of the solvent of the first supercritical extraction is in the range of 20 to 120 ml/min;
a temperature of the second supercritical extraction is in the range of 30 to 70° C.;
a pressure of the second supercritical extraction is in the range of 70 to 650 bar; and
a duration of the second supercritical extraction is in the range of 45 to 300 minutes.

11. The method of claim 8, wherein the oil is an isolated squalene.

* * * * *